United States Patent [19]

Nissen et al.

[11] 4,212,825

[45] Jul. 15, 1980

[54] ALDOL CONDENSATION AND HYDROGENATION PROCESS USING A CATALYST OF NICKEL AND COBALT TOGETHER WITH ZINC OXIDE AND ANOTHER METAL OF GROUPS VIII, IIB, IIIA, IVA AND VA OF THE PERIODIC TABLE

[75] Inventors: Axel Nissen, Leimen; Gerd Heilen, Frankenthal; Ekkehard Sapper, Ludwigshafen; Werner Fliege, Otterstadt; Arnold Wittwer, Ludwigshafen, all of Fed. Rep. of Germany

[73] Assignee: BASF Aktiengesellschaft, Fed. Rep. of Germany

[21] Appl. No.: 851,934

[22] Filed: Nov. 16, 1977

Related U.S. Application Data

[62] Division of Ser. No. 802,112, May 31, 1977, abandoned.

[30] Foreign Application Priority Data

Jun. 5, 1976 [DE] Fed. Rep. of Germany ....... 2625541

[51] Int. Cl.² .......................................... C07C 45/00
[52] U.S. Cl. .................................. 568/313; 568/390; 568/700; 568/800

[58] Field of Search ........... 260/593 R, 593 E, 590 R, 260/586 C, 590 E, 580 C, 592

[56] References Cited

U.S. PATENT DOCUMENTS

| | | | |
|---|---|---|---|
| 3,153,068 | 10/1964 | Porter et al. | 260/593 R |
| 3,316,303 | 4/1967 | Mertzweiller et al. | 260/593 R |
| 3,542,878 | 11/1970 | Swift | 260/593 R |
| 3,948,991 | 4/1976 | Chun et al. | 260/593 R |
| 4,005,147 | 1/1977 | Fischer et al. | 260/593 R |
| 4,049,571 | 9/1977 | Nissen et al. | 260/593 R |

*Primary Examiner*—Norman Morgenstern
*Assistant Examiner*—James H. Reamer
*Attorney, Agent, or Firm*—Keil & Witherspoon

[57] ABSTRACT

Aldehydes or ketones of not less than 4 or 5 carbon atoms, respectively, are manufactured in a one stage process in the liquid phase by subjecting aldehydes and/or ketones of not less than 2 or 3 carbon atoms, respectively, to an aldol condensation and hydrogenating the resulting olefinically unsaturated aldehyde, the catalyst used for the aldol condensation and hydrogenation containing a mixture of nickel and cobalt, zinc oxide and at least one of the elements iron, arsenic, antimony, bismuth, gallium, indium, thallium, germanium, tin, lead, cadmium and mercury or compounds of the said elements.

9 Claims, No Drawings

ALDOL CONDENSATION AND HYDROGENATION PROCESS USING A CATALYST OF NICKEL AND COBALT TOGETHER WITH ZINC OXIDE AND ANOTHER METAL OF GROUPS VIII, IIB, IIIA, IVA AND VA OF THE PERIODIC TABLE

This is a division of application Ser. No. 802,112 filed May 31, 1977, now abandoned.

The present invention relates to a catalyst containing zinc and a mixture of nickel and cobalt, preferably with a carrier, and to the manufacture of the catalyst, the catalyst being used for the production of $\alpha\beta$-unsaturated aldehydes and ketones and their simultaneous hydrogenation to give the corresponding saturated aldehydes and ketones and having a high selectivity; the activity of the catalyst is reduced (i.e. the catalyst is partially poisoned) by means of a specific additive.

The direct manufacture of a higher saturated ketone from an aldehyde or ketone and a ketone (e.g. of 2-methyloctan-3-one from butanal and methyl isopropyl ketone in accordance with equation (1))

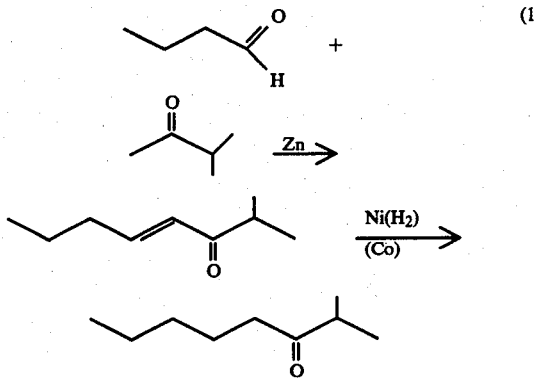

is conventionally carried out with a supported catalyst which contains zinc oxide as the aldolizing component and nickel (with or without cobalt and copper) as the hydrogenating component.

From the point of view of the success of the reaction it is immaterial whether the aldolizing component and the hydrogenating component are present on separate catalyst constituents or are homogeneously distributed, i.e., on the same catalyst particles. Where they are separate, the catalyst is also referred to as a mixed catalyst.

The reaction is in most cases carried out in the gas phase, though if it is carried out in the liquid phase a higher catalyst life is achievable than in the gas phase. This is related to the fact that in the liquid phase the hydrogenation of the double bond of the $\alpha\beta$-unsaturated ketone formed as an intermediate as a rule takes place simultaneously with the hydrogenation of the carbonyl groups contained in the reaction medium (in particular both the carbonyl groups of the newly formed ketone and those of the aldehyde and ketone initially employed). However, the intention is that these carbonyl groups should remain.

According to F. Zymalkowski: Katalytische Hydrierung (P. Enke Verlag, Stuttgart 1965, page 84), zinc ions used as additives to metals of group VIII of the periodic table of the elements (i.e. as additives to transition metals) result in a hydrogenation of the carbonyl group, whilst the double bond is preserved, i.e. result in the converse of the reaction course which is the object of the present invention.

If the process is carried out in the liquid phase, which industrially is advantageous, the presence of zinc oxide at the temperature of from 180° to 200° C. required for the reaction does indeed result in substantial hydrogenation of the carbonyl groups contained in the reaction medium, so that undesired alcohols are obtained as the main product and in many cases no aldol compounds are obtained.

It is true that in gas phase reactions hydrogenation catalysts of group VIII, in the presence of divalent zinc (e.g. as zinc oxide) appear preferentially to hydrogenate the double bond, since the disclosed hydrogenations of $\alpha,\beta$-unsaturated ketones and direct processes of the above type are, where the catalyst system contains a metal of group VIII together with zinc oxide, preferably carried out in the gas phase; in this context, attention is drawn to Japanese Published Pat. No. 72/15,180. British Pat. No. 1,328,143 (in which a mixture of saturated ketone and saturated alcohol is obtained) and German Laid-Open Application DOS No. 2,023,512.

Accordingly, it is an object of the invention to provide a catalyst for the manufacture of aldehydes or ketones of 4 or 5, respectively, or more carbon atoms by aldol condensation of low molecular weight aldehydes or ketones with low molecular weight aldehydes or ketones and hydrogenation of the intermediate $\alpha,\beta$-unsaturated aldehydes or ketones in the liquid phase.

We have found that the above object is achieved and that a catalyst which is outstandingly suitable for the envisaged process and which essentially contains (a) nickel and cobalt, (b) zinc oxide and optionally a (chemically inert) carrier and does not require any pretreatment, is obtained if the composition used to manufacture the catalyst (the catalyst precursor), which contains compounds of nickel and cobalt, zinc and, preferably, a carrier, is additionally provided with (c) a catalytically active amount of a compound of a metal of the group comprising iron, arsenic, antimony, bismuth, gallium, indium, thallium, germanium, tin, lead, cadmium and mercury and is converted to the active form, e.g. in the conventional manner (i.e. by reduction). As may be seen, the effective additives are compounds of elements of groups VIII, IIb, IIIa, IVa and Va of the periodic table of the elements. Heavy metals, i.e. metals having, in elemental form, a density of more than 5 kg/cm³, are particularly suitable.

A "catalytically active amount" is in general from 0.0001 to 10% of oxide, based on the total weight. For example, in the case of iron it is from about 0.1 to 5% whilst on the other hand, for example, lead is very active even in traces (less than 0.1%). The advantageous amount in each case is therefore suitably determined experimentally. It is assumed that the additive results in passivation (partial poisoning).

The catalyst according to the invention gives the saturated aldehyde or ketone (e.g. 2-methyloctan-3-one from butanal and methyl isopropyl ketone) as the essential product of the reaction, the raw materials being virtually completely converted. It is particularly surprising that the catalyst should make it possible to carry out aldol condensation of aldehydes with one another, the known catalysts normally being more or less unsuitable for aldehyde manufacture.

The following are details regarding the manufacture of compositions according to the invention for the purpose of manufacturing the catalyst:

Nickel and cobalt compounds and the additives according to the invention, with or without other modifiers, are processed separately or conjointly with a zinc compound, in the conventional manner, to give a catalyst composition. In general, a chemically substantially inert carrier, which may be, for example γ-alumina or some other inert carrier, in a suitable form (extrudates, spheres, granules or the like), is treated with soluble compounds of the catalytically active metals, or alternatively these are coprecipitated, kneaded together or otherwise combined with a carrier precursor. The preferred method is to absorb nickel and cobalt compounds together with a zinc compound on the carrier (i.e. to impregnate the carrier, which is a porous material), calcine and reduce the product and then apply the additives according to the invention. After the conventional pre-treatment (heating, annealing and reducing, e.g. in a stream of hydrogen), which may or may not be repeated, the composition is ready for use as a catalyst. Suitable compositions contain, for example, from 3 to 50% (expressed as metal) of nickel and cobalt, whilst the carrier advantageously consists of alumina, titanium dioxide or zirconium dioxide. Silica, pumice and other silicates have hitherto been less convincingly successful.

The zinc content (calculated as oxide) is, for example, from 1 to 10%, given an appropriate carrier as described above; it it assumed that the zinc is present as zinc oxide.

The use of unsupported nickel and/or cobalt catalysts is in principle possible but apparently of no particular advantage and therefore generally uncommon, for economic reasons.

The overall mode of action of the catalyst is surprising because, according to prevailing views, iron ions, for example, favor the hydrogenation of carbonyl groups to give the alcohol. This is mentioned on page 82 of the book by Zymalkowski, cited above.

The suitable reaction conditions for the new catalyst to be effective in general do not differ from those chosen for conventional catalysts; the carbonyl compounds are reacted and at the same time the converted (aldolized) reaction mixture is hydrogenated at from above 150° C. to about 250° C. under a total pressure of, for example, from 5 to 100 bars, the hydrogen partial pressure being, for example, from 0.5 to 80 bars. In general, extraneous solvents are not necessary provided a sufficiently high pressure is selected and the physical properties of the reactants permit this. The presence of solvents, even of minor amounts of water, in general however has no effect on the conduct of the reaction. It is advantageous to use an excess of one of the reactants, which then acts as a solvent.

The invention of the catalyst is related to the manufacture of unsaturated and, as a further step, saturated aldehydes and ketones.

The actual object of the invention is to provide an advantageous process for the manufacture of carbonyl compounds, i.e. of aldehydes and ketones. In general, the compounds to be manufactured are known compounds.

For example, the invention may be used advantageously to manufacture aldehydes and ketones of the general formula $$R^1-CO-R^2$$

where $R^1$ and/or $R^2$ is straight or branched alkyl, cycloalkyl, aryl or aralkyl, $R^2$ may also be hydrogen and the sum of the carbon atoms of $R^1$ and $R^2$ is not less than 3 (aldehydes) or 4 (ketones). Where $R^1$ and/or $R^2$ is aryl or aralkyl, these may carry chemically inert substituents, e.g. methoxy. At least one radical is advantageously of not less than 3 carbon atoms. Generally, aldehydes and ketones with a total of more than 20 carbon atoms, including that of the carbonyl group, are industrially of less interest, though they can be synthesized in accordance with the invention.

The starting materials generally used for such carbonyl compounds are therefore aldehydes (especially with terminal aldehyde groups) of, for example, 2 to 17 carbon atoms or ketones of, for example, 3 to 17 carbon atoms. They can be condensed with each other or with themselves in optional combination, in accordance with conventional rules. Advantageously, the starting ketone contains a keto group of the structure —CO—CH$_3$, i.e. it possesses an isolated methyl group connected to the keto group.

Examples of suitable aldehydes are acetaldehyde, propionaldehyde, n- and i-butyraldehyde, pentanal-1, 2-methylbutanal, 2-methylpentanal, 3-methylbutanal, cyclohexylaldehyde, benzaldehyde, vanillin and veratraldehyde.

Examples of suitable ketones are acetone, methyl ethyl ketone, methyl isopropyl ketone, 4-methylheptan-2-one, acetophenone and other straight or branched ketones, especially saturated ketones, which have the keto group in the 2-position.

On the other hand, in the reaction between an aldehyde, on the one hand, and a ketone, on the other, it is advantageous to have present a less than stoichiometric amount of the aldehyde to be used, if it is important that the reaction should give substantially one product. If the aldehyde is present in excess, the new ketone already formed as a rule participates in the reaction, especially if the starting ketone is acetone, so that to a certain extent a further ketone, which in turn has a longer chain, is formed as a by-product. Since, however, the mixture of compounds obtained can in general be separated easily, it is also possible to proceed differently, for example for economic reasons.

Unless stated otherwise, amounts mentioned in the Examples which follow are by weight.

EXAMPLE 1

A catalyst which contains 8% by weight of nickel, 8% by weight of cobalt and 8% by weight of zinc oxide (the remainder being Al$_2$O$_3$) is manufactured in the conventional manner. γ-Al$_2$O$_3$ extrudates of 4 mm diameter are impregnated with an aqueous solution of the nitrates, dried at 120° C. and calcined at 520° C. The reduction with hydrogen is carried out at 300° C. The composition thus prepared is impregnated with a catalytic amount of an aqueous solution of Fe(NO$_3$)$_3$, again dried, calcined and reduced with hydrogen.

The finished catalyst contains 8% by weight of nickel, 8% by weight of cobalt, 8% by weight of zinc oxide and 2% by weight of iron oxide (calculated as Fe$_2$O$_3$), based on γ-Al$_2$O$_3$. It is filled into a tubular reactor. On passing a mixture of 76% of acetone and 24% of methylpropanal at 180° C., under a pressure of 20 bars (of hydrogen), over the catalyst in an amount of 1 liter of mixture per liter of catalyst per hour a reaction mixture which, according to analysis by gas chromatography, has the composition shown below (Table 1; the water formed in the reaction is left out of account) is obtained:

TABLE 1

| | | |
|---|---|---|
| Acetone | 60.5% by weight | ⎫ unconverted |
| Methylpropanal | 5.3% by weight | ⎬ starting |
| Isopropanol | 0.3% by weight | ⎭ materials |
| Methylpropanol | 4.2% by weight | |
| 4-Methylpentan-2-one | 2.0% by weight | |
| 4-Methyl-3-penten-2-one | 0.6% by weight | |
| 5-Methylhexan-2-one | 20.1% by weight | |
| 5-Methyl-3-hexen-2-one | 0.9% by weight | |
| 2,8-Dimethylnonan-5-one | 1.8% by weight | |
| 2,8-Dimethyl-3-nonen-5-one | ⎫ 0.7% by weight | |
| 2,8-Dimethyl-3,6-nonadien-5-one | ⎭ | |

EXAMPLE 2

A mixture of 73% by weight of acetone and 27% by weight of 3-methylbutanal is reacted, under the same conditions as those used in Example 1, over a catalyst manufactured as described above, which contains, as active constituents, 8% by weight of nickel, 8% by weight of cobalt, 8% by weight of zinc (as ZnO) and 2% of antimony (as $Sb_2O_3$) on alumina. The resulting reaction mixture has the following composition (Table 2), the water formed being left out of account:

TABLE 2

| | | |
|---|---|---|
| Acetone | 58.0% by weight | ⎫ Unconverted |
| 3-Methylbutanal | 4.0% by weight | ⎬ starting |
| Isopropanol | 0.7% by weight | ⎭ materials |
| 3-Methylbutanol | 1.9% by weight | |
| 4-Methylpentan-2-one | 1.3% by weight | |
| 4-Methyl-3-penten-2-one | 0.9% by weight | |
| 6-Methylheptan-2-one | 24.0% by weight | |
| 6-Methyl-3-hepten-2-one | 1.3% by weight | |
| 2,10-Dimethylundecan-6-one | 2.6% by weight | |
| 2,10-Dimethyl-4-undecen-6-one | ⎫ 1.2% by weight | |
| 2,10-Dimethyl-4,7-undecadien-6-one | ⎭ | |

EXAMPLE 3

A mixture of 66% by weight of acetone and 34% by weight of benzaldehyde is reacted, under the conditions of Example 1, over a catalyst manufactured as described in Example 1 (active constituents 8% by weight of nickel, 8% by weight of cobalt, 8% by weight of zinc (as ZnO) and 3% by weight of tin (as SnO)). The reaction mixture obtained has the following composition (Table 3), the water formed being kept out of account:

TABLE 3

| | |
|---|---|
| Acetone | 49.8% by weight |
| Benzaldehyde | 4.0% by weight |
| Isopropanol | 0.6% by weight |
| 4-Methylpentan-2-one | 3.2% by weight |
| 4-Methyl-3-penten-2-one | 2.0% by weight |
| Benzyl alcohol | 4.1% by weight |
| 4-Phenylbutan-2-one | 24.1% by weight |
| 4-Phenyl-3-buten-2-one | 2.8% by weight |
| 1,5-Diphenylpentan-3-one | 4.2% by weight |
| 1,5-Diphenyl-1-penten-3-one | ⎫ 1.4% by weight |
| 1,5-Diphenyl-1,4-pentadien-3-one | ⎭ |

EXAMPLE 4

The catalyst examined in this Example contains the following active constituents: 8% by weight of nickel, 8% by weight of cobalt, 8% by weight of zinc and 5% of $Bi_2O_3$; as described above, a mixture of 80% by weight of acetophenone and 20% by weight of propionaldehyde is reacted. The reaction mixture has the following composition (Table 4):

TABLE 4

| | |
|---|---|
| Acetophenone | 51.3% by weight |
| Propionaldehyde | 4.1% by weight |
| 1-Phenylethanol | 4.2% by weight |
| n-Propanol | 4.0% by weight |
| 1-Phenylpentanone | 18.8% by weight |
| 1-Phenyl-2-pentenone | 4.0% by weight |

EXAMPLES 5 TO 8

Various catalysts, each of which was obtained in the conventional manner by simultaneously impregnating the carrier ($\gamma$-$Al_2O_3$) with the solutions of the nitrates of Ni, Co, Zn and one of the heavy metals according to the invention, drying, calcining and reducing, are tested. In each case, a mixture of 76% by weight of acetone with 24% by weight of n-butanal is reacted under identical conditions (see Example 1) and the results shown below (Table 5; all data are percent by weight, as previously) are obtained:

TABLE 5

| Example | Catalyst | A | B | C | D | E | F | G | H | I | K |
|---|---|---|---|---|---|---|---|---|---|---|---|
| 5 | 8% of Ni, 8% of Co, 8% of Zno, 2% of $Tl_2O_3$ | 59.2 | 4.0 | 0.4 | 4.1 | 2.3 | 0.6 | 18.8 | 2.9 | 1.9 | 0.5 |
| 6 | 8% of Ni, 8% of Co, 8% of Zno, 0.1% of CdO | 58.1 | 2.8 | 0.2 | 3.7 | 1.6 | 0.4 | 19.1 | 4.3 | 2.1 | 0.7 |
| 7 | 8% of Ni, 8% of Co, 8% of Zno, 0.01% of PbO | 58.6 | 3.1 | 0.1 | 4.7 | 1.4 | 1.2 | 17.1 | 4.7 | 1.8 | 1.1 |
| 8 | 8% of Ni, 8% of Co, 8% of Zno, 1% of $As_2O_3$ | 60.1 | 1.9 | 0.6 | 3.2 | 1.7 | 0.4 | 23.0 | 2.1 | 2.0 | 0.4 |

In the preceding Table the letters have the following meaning:
A: acetone
B: n-butanal
C: isopropanol
D: n-butanol
E: 4-methylpentan-2-one
F: 4-methyl-3-penten-2-one
G: heptan-2-one
H: 3-hepten-2-one
I: undecan-6-one
K: 4-undecen-6-one; 4,7-undecadien-6-one

COMPARATIVE EXPERIMENT

A catalyst which is composed of 8% of Ni, 8% of Co and 8% of ZnO (the remainder being carrier), and which does not contain any further additives, is used. The reaction mixture and conditions correspond to Example 1. The converted reaction mixture has the following composition:

TABLE

| | |
|---|---|
| Acetone | 8% by weight |
| Methylpropanal | 8% by weight |
| Isopropanol | 8% by weight |
| Methylpropanol | 2% by weight |
| 4-Methylpentan-2-one | 6% by weight |
| 4-Methyl-3-penten-2-one | 8% by weight |
| 5-Methylhexen-2-one | 8% by weight |
| 5-Methyl-3-hexen-2-one | 2% by weight |
| 2,8-Dimethylnonan-5-one | 4% by weight |
| 2,8-Dimethyl-3-nonen-5-one | not determined |
| 2,8-Dimethyl-3,6-nonadien-5-one | |

We claim:

1. In a process for the manufacture of a saturated carbonyl compound by aldol condensation of a low molecular weight aldehyde or ketone of not less than 2 or 3 carbon atoms, respectively, with itself or with another such low molecular weight aldehyde or ketone and hydrogenation of the aldol condensation product at above 150° C. in the liquid phase and in the presence of a catalyst, the improvement which comprises:
    carrying out said condensation and hydrogenation with said catalyst consisting essentially of the components:
    (a) nickel and cobalt compounds;
    (b) zinc oxide; and
    (c) a catalytically active amount of a compound of a metal selected from the group consisting of iron, arsenic, antimony, bismuth, gallium, indium, thallium, germanium, tin, lead, cadmium and mercury, said components being applied to a chemically inert carrier and said components being obtained in a catalytically active form by drying the catalyst, calcining at about 520° C. and reducing with hydrogen at about 300° C.

2. A process as claimed in claim 1 wherein the insert carrier for the catalyst is alumina, titanium dioxide or zirconium oxide.

3. A process as claimed in claim 2 wherein the reaction is carried out at 150° to 250° C. and 5 to 100 bars with a hydrogen partial pressure of 0.5 to 80 bars.

4. A process as claimed in claim 1 wherein the inert carrier for the catalyst is alumina and the reaction is carried out at 150° to 250° C. and 5 to 100 bars with a hydrogen partial pressure of 0.5 to 80 bars.

5. A process as claimed in claim 1 wherein the aldehyde reactant is selected from the group consisting of acetaldehyde, propionaldehyde, n- and i-butyraldehyde, pentanal-1, 2-methylbutanal, 2-methylpentanal, 3-methylbutanal, cyclohexylaldehyde, benzaldehyde, vanillin and veratraldehyde, and the ketone reactant is selected from the group consisting of acetone, methyl ethyl ketone, methyl isopropyl ketone, 4-methylheptan-2-one and acetophenone.

6. A process as claimed in claim 1, wherein an aldehyde of 2 to 17 carbon atoms is reacted with itself or another aldehyde of 2 to 17 carbon atoms.

7. A process as claimed in claim 1, wherein a ketone of 3 to 17 carbon atoms is reacted with itself or with another ketone of 3 to 17 carbon atoms.

8. A process as claimed in claim 1, wherein an aldehyde of 2 to 17 carbon atoms is reacted with a stoichiometric excess of a ketone of 3 to 17 carbon atoms.

9. A process as claimed in claim 1, wherein the reaction is carried out at 150° to 250° C. and 5 to 100 bars with a hydrogen partial pressure of 0.5 to 80 bars.